US012582793B2

(12) United States Patent
Herrmann

(10) Patent No.: US 12,582,793 B2
(45) Date of Patent: Mar. 24, 2026

(54) PUMP DEVICE, RESPIRATORY DEVICE AND METHOD FOR PROVIDING A RESPIRATORY GAS

(71) Applicant: WEINMANN EMERGENCY MEDICAL TECHNOLOGY GMBH + CO. KG, Hamburg (DE)

(72) Inventor: Frank Herrmann, Barmstedt (DE)

(73) Assignee: WEINMANN EMERGENCY MEDICAL TECHNOLOGY GMBH + CO. KG, Hamburg (DE)

( * ) Notice: Subject to any disclaimer, the term of this patent is extended or adjusted under 35 U.S.C. 154(b) by 646 days.

(21) Appl. No.: 18/011,783

(22) PCT Filed: Apr. 21, 2021

(86) PCT No.: PCT/DE2021/100368
§ 371 (c)(1),
(2) Date: Dec. 20, 2022

(87) PCT Pub. No.: WO2022/002291
PCT Pub. Date: Jan. 6, 2022

(65) Prior Publication Data
US 2023/0330380 A1     Oct. 19, 2023

(30) Foreign Application Priority Data

Jul. 1, 2020    (DE) ..................... 10 2020 117 343.1

(51) Int. Cl.
*A61M 16/10*     (2006.01)
*A61B 5/087*     (2006.01)
(52) U.S. Cl.
CPC ......... *A61M 16/107* (2014.02); *A61B 5/0875* (2013.01); *A61M 2202/02* (2013.01)

(58) Field of Classification Search
CPC ............ A61M 16/107; A61M 2202/02; A61B 5/0875
See application file for complete search history.

(56) References Cited

U.S. PATENT DOCUMENTS 6,203,301 B1     3/2001  Kim
2007/0251245 A1*  11/2007  Sakitani ................ F04C 18/322
                                                          62/6
(Continued)

FOREIGN PATENT DOCUMENTS

AT           200247 B      10/1958
AT           314724 B       4/1974
(Continued)

OTHER PUBLICATIONS

English Translation CN 105422444 A (Year: 2016).*
International Search Report Dated Jul. 28, 2021, PCT/DE2021/100368, 3 Pages.

*Primary Examiner* — Shafiq Mian
(74) *Attorney, Agent, or Firm* — LUCAS & MERCANTI, LLP; Klaus P. Stoffel

(57)     ABSTRACT

A pump device, a respiratory device and a method for providing a respiratory gas. A specially formed rotor and a corresponding pump chamber are used so that an approximately sinusoidal flow of an out-flowing fluid is possible. With the combination of two pump chambers with rotors driven in a 180° phase-shifted manner to one another, an almost constant flow can be created at a common outlet. In addition, the system is designed to be highly dynamic with simultaneously relatively low energy consumption.

11 Claims, 7 Drawing Sheets

(56)　　　　　References Cited

U.S. PATENT DOCUMENTS

| | | | |
|---|---|---|---|
| 2011/0058970 A1 | 3/2011 | Hugenroth | |
| 2011/0247620 A1* | 10/2011 | Armstrong ........ | A61M 16/0677 |
| | | | 128/207.18 |
| 2014/0219845 A1* | 8/2014 | Hugenroth ........ | A61M 16/0057 |
| | | | 418/13 |

FOREIGN PATENT DOCUMENTS

| | | | | |
|---|---|---|---|---|
| CN | 101387295 A | 3/2009 | | |
| CN | 105422444 A * | 3/2016 | ............. | F04C 15/06 |
| DE | 4205838 A1 | 9/1992 | | |
| DE | 19980588 C2 | 5/2002 | | |
| EP | 1486677 A1 | 12/2004 | | |
| EP | 1780478 B1 | 12/2016 | | |
| EP | 3597923 A1 | 1/2020 | | |

* cited by examiner

*angle of rotation (°)*

FIG.12

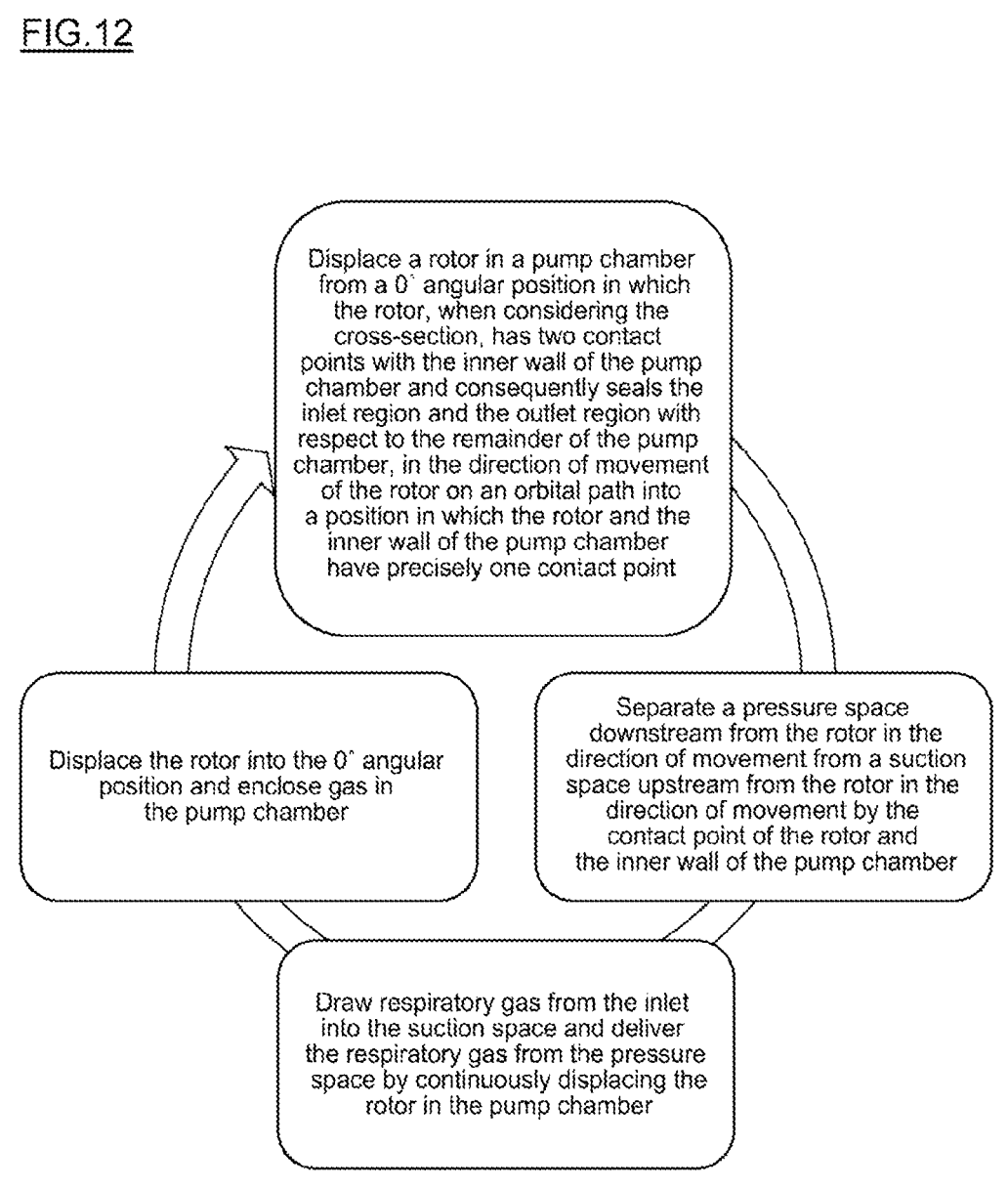

Displace a rotor in a pump chamber from a 0° angular position in which the rotor, when considering the cross-section, has two contact points with the inner wall of the pump chamber and consequently seals the inlet region and the outlet region with respect to the remainder of the pump chamber, in the direction of movement of the rotor on an orbital path into a position in which the rotor and the inner wall of the pump chamber have precisely one contact point Separate a pressure space downstream from the rotor in the direction of movement from a suction space upstream from the rotor in the direction of movement by the contact point of the rotor and the inner wall of the pump chamber Draw respiratory gas from the inlet into the suction space and deliver the respiratory gas from the pressure space by continuously displacing the rotor in the pump chamber Displace the rotor into the 0° angular position and enclose gas in the pump chamber

PUMP DEVICE, RESPIRATORY DEVICE AND METHOD FOR PROVIDING A RESPIRATORY GAS

CROSS-REFERENCE TO RELATED APPLICATIONS

The present application is a 371 of International application PCT/DE2021/100368, filed Apr. 21, 2021, which claims priority of DE 10 2020 117 343.1, filed Jul. 1, 2020, the priority of these applications is hereby claimed and these applications are incorporated herein by reference.

BACKGROUND OF THE INVENTION

The invention relates to a pump device within the sense of a positive-displacement pump, in particular designed for delivering gases.

The invention furthermore relates to a respiratory device having such a pump device.

The invention moreover relates to a method for providing respiratory gas with the aid of a respiratory device.

There are various specific requirements for effectively implementing ventilation when mechanically ventilating patients with the aid of respiratory devices.

In extreme ventilation situations, for example in the case of a minute volume V˙=10 L/min and a maximum pressure increase $\Delta p=60$ hPa, the average pneumatic power $P_{average}=$*$\Delta p=1$ W, as a result of which the pneumatic power demand is low. The requirements intensify in the case of intermittent operation in which a short in-breath is accompanied by rapid pressure rises and high flows. Although the peak flows required here of up to V˙=180 L/min and pressure increases of up to $\Delta p=180$ hPa/s entail higher pneumatic peak power, the average pneumatic power remains within a low range of a few watts.

In order to generate the required flows and pressures, known respiratory devices generally have fans which draw the air in via an inlet and deliver it through an outlet with the aid of a fan impeller rotating in a fan. Fans of this type offer various advantages such as a compact and simple structure, a high flow rate, and high dynamics and also represent an almost ideal pressure source. However, a larger speed stroke is necessary to build up the pressure, the suitability as a flow source is rather low, the highly turbulent flow of the emerging fluid makes it hard to measure the flow downstream, and the average pneumatic overall efficiency is significantly below 10%. In detail, rapid rises in speed with accompanying rises in pressure cause a significant change in the rotational energy stored in the fan impeller, for which high power is required. This power requirement lies in a range above 40 W and can be much higher in the case of very rapid required rises in pressure. There is furthermore a high static power requirement in the case of a high speed. As a result, a very large amount of heat is created overall when using fans in respiratory devices, it being necessary to dissipate this heat such that cooling measures are imperative.

As alternatives to fans, the prior art includes in particular piston pumps and diaphragm pumps for use in respiratory devices which, although they enable to some extent lower turbulence of the outflowing fluid and lower heat loss, because of their construction they place particularly high demands on the component tolerances such that the production costs for an appropriately precise dimensioning of the components are increased.

SUMMARY OF THE INVENTION

An object of the invention is to provide a pump device which, compared with a fan, has improved properties in terms of power consumption and heat output.

A further object of the invention is to provide a pump device which, compared with a fan, enables lower turbulence of the emerging fluid.

A further object of the invention is to provide a pump device which places lower demands on the component tolerances.

A further object of the invention is to provide an improved respiratory device.

A further object of the invention is to provide an improved method for providing respiratory gas.

The features of a pump device which are disclosed below are part of the invention both individually and in all feasible combinations.

A pump device according to the invention is designed as a positive-displacement pump and has at least one pump chamber and, for each pump chamber, a rotor arranged therein.

The pump chamber is arranged in a housing and is designed as a stator of the pump device.

The pump chamber has an inlet and an outlet through which a fluid can flow into the pump chamber and flow out of it, respectively.

The rotor can move inside the pump chamber, guided along the inner wall of the pump chamber.

In an embodiment of the invention, the rotor can move rotation-free inside the pump chamber, in the sense that, although the position of the rotor inside the pump chamber can be changed, its orientation cannot.

In an embodiment of the invention, the rotor or a point of the rotor can move so that it is guided on an orbital path.

In an embodiment of the invention, the rotor is mounted eccentrically on a rotatable shaft of a drive means and is decoupled from the rotation with the aid of a decoupling apparatus such that an orbital movement of the rotor can be implemented.

In an embodiment of the invention, the decoupling apparatus takes the form of a rolling bearing.

The rotor can be moved inside the pump chamber in such a way that a suction space, into which a fluid can be drawn via the inlet by the movement of the rotor, can be formed in the pump chamber behind the rotor in the direction of movement. A pressure space, from which the fluid can be delivered out of the pump chamber via the outlet by the movement of the rotor, can be formed inside the pump chamber in front of the rotor in the direction of movement.

The suction space is defined here depending on the angular position of the rotor in the pump chamber as the volume of the pump chamber, less the volume of the rotor, which has a connection to the inlet, and the pressure space as the volume of the pump chamber, less the volume of the rotor, which has no connection to the inlet.

In an embodiment of the invention, the inlet and the outlet of the pump chamber are arranged on a common duct connected to the pump chamber. The duct is separated with the aid of a separating element into a region associated with the inlet and a region associated with the outlet.

In an embodiment of the invention, the separating element is connected to the rotor.

In an embodiment of the invention, the separating element is designed as a connecting rod, with an at least partially stem-like shape, which is connected to the rotor.

In a preferred embodiment of the invention, the connecting rod connected to the rotor projects from the pump chamber into the region of the inlet and the outlet of the pump chamber and seals the inlet with respect to the outlet.

In an embodiment of the invention, the connecting rod of the rotor is guided linearly at the end averted from the remainder of the rotor.

In an embodiment of the invention, the stator, in particular the wall of the pump chamber, is manufactured from a metal such that a high dimensional stability and thermal conductivity are provided.

In a preferred embodiment of the invention, the wall of the pump chamber is formed from aluminum which has a relatively low mass in addition to high dimensional stability and thermal conductivity.

In an embodiment of the invention, the rotor is formed from a slide-promoting plastic such that there is low friction between the rotor and the inner wall of the pump chamber.

The profile of the flow of the fluid flowing out of the outlet of the pump chamber is here directly linked to the profile of the volume of the suction or the pressure space of the pump device depending on the angular position of the rotor inside the pump chamber.

In a preferred embodiment of the invention, the rotor has at least one cavity to reduce the mass of the rotor. The smaller the mass of the rotor, the less the energy required for adapting the operating speed of the rotor.

In a preferred embodiment of the invention, the rotor is formed in relation to the inner wall of the pump chamber such that, on the orbital movement path of the rotor effected by means of the eccentric drive means, in precisely one position on the movement path, it has in cross-section two contact points with the inner wall of the pump chamber, whilst at all the other positions the rotor has in cross-section just one contact point with the inner wall of the pump chamber.

According to the three-dimensional design of the rotor and the pump chamber, overall one contact line or two contact lines are formed depending on the position of the rotor. In the case of a disk-like structure in which the rotor and the pump chamber each extend over a height h with a constantly shaped surface, the contact lines are straight lines or sections of straight lines.

In a preferred embodiment of the invention, the separating element is arranged, in the circumferential direction of the rotor, between the two contact points of the rotor and the inner wall of the pump chamber, wherein the lower spacing of the contact points in the circumferential direction is decisive.

In a particularly preferred embodiment of the invention, the path from the inlet and the path from the outlet into the remaining volume of the pump chamber are blocked in those positions in which the rotor has two contact points with the inner wall of the pump chamber such that a volume is enclosed inside the pump chamber.

The position in which the rotor and the inner wall of the pump chamber have two contact points is defined as the zero position or 0° angular position relative to the orbital movement path. The angle increases depending on the position of the rotor in its direction of movement until the zero position is reached again at the angular position of 360°.

In an embodiment of the invention, arranged in the region of the rotor is at least one spring by means of which the rotor can be pressed against the inner wall of the pump chamber such that a sealing effect at the at least one contact point between the rotor and the inner wall is improved. In particular higher manufacturing tolerances are enabled as a result.

In a different embodiment of the invention, the housing wall is configured such that the housing wall is designed so that it bears resiliently against a fixedly mounted rotor such that in particular higher manufacturing tolerances are enabled.

In an embodiment of the invention, the housing wall of the pump chamber is designed so that it is somewhat smaller than the ideal contour for the corresponding rotor and can be pressed slightly outward by the rotor at the contact point/ contact points.

In a further embodiment of the invention, the housing of the pump chamber has fins which project inward into the latter, extend transversely to the direction of movement of the rotor in the pump chamber, and contact the rotor in the region of the contact point or contact points. The pressure created in the pump chamber here presses the fins against the rotor, wherein the contact pressure of the fins is very low with no significant initial pressure.

In a further embodiment of the invention, resilient mounting of the rotor and one of the above-described embodiments of the housing of the pump chamber are combined with each other.

In a preferred embodiment of the invention, the shape of the pump chamber and the rotor are matched to each other in such a way that, with a constant speed of the rotor, a smooth profile of the flow of the delivered fluid is effected at the outlet of the pump chamber.

In a preferred embodiment of the invention, the shape of the pump chamber and the rotor are matched to each other in such a way that, with a constant speed of the rotor, an approximately sinusoidal profile of the flow of the delivered fluid is effected at the outlet of the pump chamber, wherein the minimum value of the flow is at approximately 0 (no flow in the opposite direction).

In an embodiment of the invention, the rotor has a circular design. Because of the thickness of the separating wall between the inlet and the outlet, formed in embodiments of the invention by the separating element designed for example as a connecting rod, the profile of the flow of the fluid at the outlet is, however, designed so that it deviates slightly from a sine curve.

The thinner the separating element or the stem of the connecting rod, the closer the profile of the flow of the fluid at the outlet is to a sine-wave shape. In embodiments of the invention, the separating element or the connecting rod is therefore not rigid and instead is designed as a thin separating layer which is connected to the housing of the pump device at the end averted from the rotor, sealing the inlet from the outlet.

The separating element or the connecting rod and/or the sealing connection of the separating element or connecting rod and the housing here has a flexible design such that the movement of the rotor on the orbital path is not disturbed.

The volume that can be delivered by the pump device in one revolution of the rotor is dependent on the eccentricity of the rotor, wherein the pump volume increases as the eccentricity increases. The reason for this is that the orbital path of the rotor is lengthened as the eccentricity increases such that the size of the pump chamber also has to be adapted accordingly.

A disadvantage of a circular rotor is that only a small eccentricity is possible for an optimally sinusoidal profile of the flow of a fluid flowing out from the outlet such that only a small pump volume can be achieved. In order to address these problems, in preferred embodiments of the invention the shape of the rotor is adapted so that it departs from a circle.

In a preferred embodiment of the invention, the rotor has a circular basic shape which is widened by circles, with a smaller diameter than the circular basic shape, arranged in each case laterally adjoining the separating element and partially projecting beyond the circular basic shape. The transitions between the basic shape and the smaller circles are here made uninterruptedly at least on the sides averted from the separating element.

In a further embodiment of the invention, the rotor according to the previous embodiment has an elliptical basic shape as its basic shape instead of a circle, wherein that half of the ellipse facing the separating element is modified by two circles which partially overlap each other and the transition of the ellipse into the circles is configured as a smooth one.

In a different embodiment of the invention, the shape of the rotor is designed according to a spline function.

Spline functions can be used advantageously to form the rotor because they enable a smooth curve profile. By generating a spline function in Cartesian coordinates and converting it into polar coordinates (radius over angle), as many smooth rotor curves as desired can be formed which can be further optimized in terms of the flow profile.

The approximately sinusoidal profile of the out-flowing fluid is effected in an embodiment of the invention by a free cross-section, extending approximately sinsuoidally, in the region of the outlet or the connection of the outlet to the pump chamber whilst the rotor is revolving in the pump chamber.

The shape of the rotor and the shape of the pump chamber are in preferred embodiments of the invention symmetrical at 0° and 180° angular positions with respect to the axis connecting the angles 0°-180°.

In a preferred embodiment of the invention, the pump device has two rotors, running phase-shifted by 180° with respect to the angular position on their orbital paths, each in a pump chamber for an overall almost constant volume flow of the fluid at a common outlet.

In an advantageous embodiment of the invention, this is effected by superimposing two approximately sinusoidal flow profiles, phase-shifted by 180°, of the individual pump chamber/rotor arrangements.

In a preferred embodiment of the invention, the rotors can be driven eccentrically on a common shaft such that very good balancing of masses and a virtually pulsation-free overall flow are enabled.

In addition, the vibration of the pump device is reduced by the balancing of masses.

A respiratory device according to the invention has at least one pump device according to the above description for delivering the respiratory gas.

In a preferred embodiment of a respiratory device according to the invention, the latter has a pump device with two rotors, oriented offset by 180° with respect to their angular position, each in a pump chamber, by means of which a virtually pulsation-free profile of the flow of the respiratory gas is effected at a common outlet.

In an embodiment of a respiratory device according to the invention, the latter furthermore has a flow measurement apparatus for measuring the volume flow of the respiratory gas.

In a preferred embodiment of a respiratory device according to the invention, the latter has a regulating device for regulating the flow of the respiratory gas at the outlet of the pump device. In particular, to do this, the speed of the eccentric drive of the at least one rotor of the pump device can be controlled with the aid of a control unit.

The features disclosed below of a method for providing respiratory gas are part of the invention, both individually and in all feasible combinations.

A method according to the invention for providing respiratory gas has at least the following method steps:

Displace a rotor in a pump chamber from a 0° angular position, in which the rotor has two contact points with the inner wall of the pump chamber and consequently seals the inlet region and the outlet region relative to the remainder of the pump chamber (pressure space), in the direction of movement of the rotor on an orbital path, into a position in which the rotor and the inner wall of the pump chamber have precisely one contact point, separate a pressure space in front of the rotor in the direction of movement and a suction space behind the rotor in the direction of movement by the contact point of the rotor and the inner wall of the pump chamber, draw respiratory gas from the inlet into the suction space, and deliver the respiratory gas from the pressure space via the outlet by continuous displacement of the rotor in the pump chamber, wherein the same method steps are implemented in a sequence phase-shifted by 180° with a second rotor in a second pump chamber such that, when the rotors circulate on the respective orbital paths inside the respective pump chamber at a constant running speed, an optimally smooth flow profile of the respiratory gas is achieved at a common outlet.

In a preferred embodiment of the method according to the invention, the flow of the respiratory gas is regulated by a control system of the speed of movement of the rotors.

In an advantageous embodiment of the method according to the invention, a pump device according to the invention or a respiratory device according to the invention having a pump device according to the invention is used according to the above description.

In advantageous embodiments, the invention has at least the following advantages and properties:

A low (mass) inertia in the system for low-energy pressure/flow change.

A low power demand with a constant pressure or flow

Possibility of pressure- and/or flow-controlled ventilation

A compact structure with a low weight.

An achievable pressure increase of at least $\Delta p = 60$ hPa·

An achievable pressure rise of $\Delta p = 180$ hPa/s

A peak flow of $$V^* = 180 \ \frac{L}{min}$$

A highly dynamic and at the same time energy-saving system is enabled by the low rotational energy in the system according to the invention. It is ideally possible to maintain the pressure without moving the rotor or rotors. The demands on the system cooling are less than in the case of a fan because the highest energy demand is needed for changing the rotational energy and this is lower in a system according to the invention. In contrast to the fan, the flow of the out-flowing fluid is less turbulent, as a result of which advantages are afforded for downstream flow measurement.

The above described construction principle according to the invention can optionally also be applied for compressors or for vacuum pumps.

BRIEF DESCRIPTION OF THE DRAWING

Exemplary embodiments of the invention are illustrated in the drawings, in which:

FIG. 12 shows a flow diagram of a method according to the invention for providing respiratory gas.

DETAILED DESCRIPTION OF THE INVENTION

Figure 1:
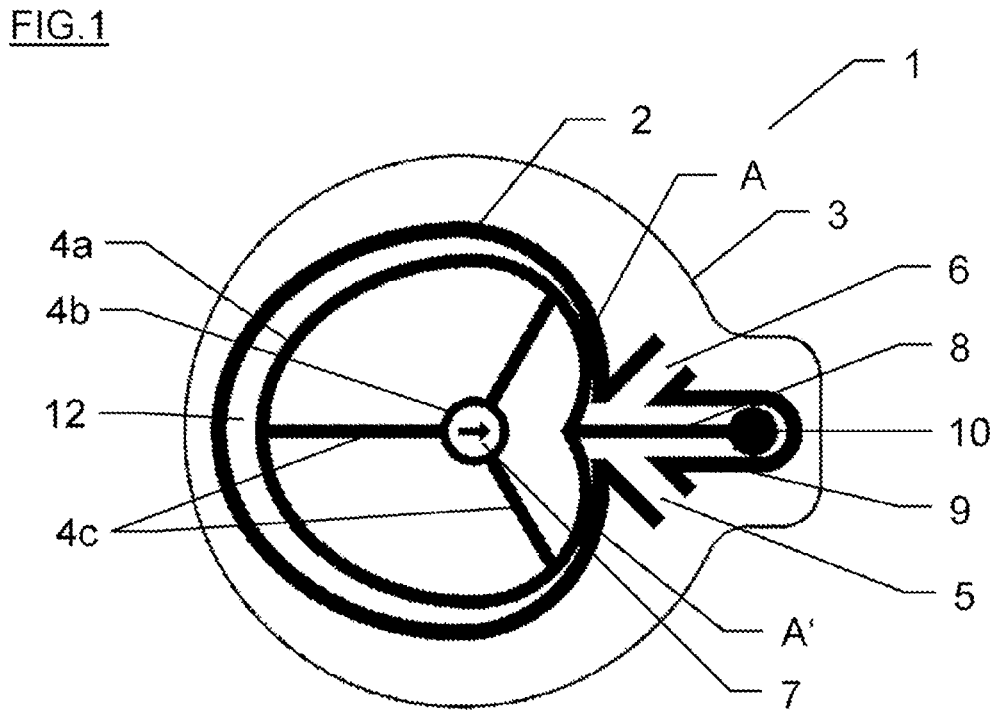
FIG. 1 shows a cross-section of a pump device according to the invention in the region of the pump chamber in the 0° angular position of the rotor.

FIG. 1 shows in a schematic illustration a section through an embodiment according to the invention of a pump device (1). The pump device (1) has a pump chamber (2) which is integrated into a housing (3). A rotor (4) is arranged in the pump chamber (2). The rotor (4) has a rotor wall (4a), a rotor core (4b), and spokes (4c) which connect the rotor core (4b) to the rotor wall (4a). This structure makes it possible for the rotor (4) to be configured so that it is internally hollow such that the mass of the rotor (4) is low. The pump chamber (2) has an inlet (5) and an outlet (6), wherein a fluid can flow into the pump chamber (2) through the inlet (5) and can flow out of the pump chamber (2) through the outlet (6). The rotor (4) can be moved inside the pump chamber (2) with the aid of a drive means (7). The drive means (7) is preferably designed as an eccentric drive means such that the rotor (4) can be moved in the pump chamber (2) on an orbital path. On the right-hand side, the rotor (4) has a separating element (8) designed as a connecting rod by means of which the region of the inlet (5) is separated from the region of the outlet (6). At its end averted from the remainder of the rotor (4), the separating element (8) has a sealing element (10) which is guided linearly in a guide (9). The region of the inlet (5) is sealed from the region of the outlet (6) in the region of the guide (9) with the aid of the sealing element (10). The angular position of the rotor (4), which is here the zero position, is indicated by the arrow in the region of the drive means (7). In the zero position or the 0° angular position, the rotor (4) has two contact points (A, A') with the inner wall of the pump chamber (2). The pressure space (12) formed between the rotor wall (4a) and the inner wall of the pump chamber (2) in this position in the pump chamber (2)

is separated from the outlet (6) by the first contact point (A) and from the inlet (5) by the second contact point (A').

The shapes of the rotor (4) and the pump chamber (2) are matched to each other in such a way that the profile of the volume flow or flow of a fluid flowing out of the outlet (6) of the pump device (1) is approximately sinusoidal at a constant speed of movement of the rotor (4). On the left-hand side, the contour of the rotor wall (4a) corresponds approximately to the contour of an ellipse with a first diameter, and on the right-hand side to two overlapping circles with a smaller diameter. The first circle here merges into the two smaller circles.

Figure 2:
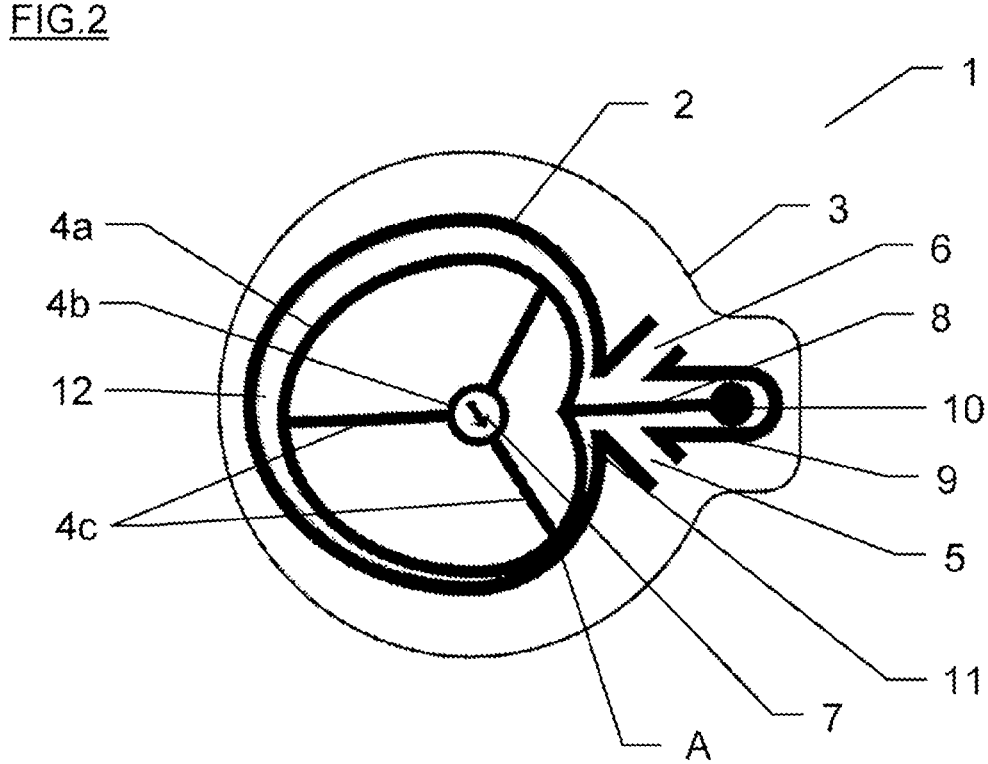
FIG. 2 shows a cross-section of a pump device according to the invention in the region of the pump chamber in the 60° angular position of the rotor.

The pump device (1) shown in FIG. 1 is illustrated in FIG. 2 in an angular position of approximately 60°. The rotor (4) and the inner wall of the pump chamber (2) now have just one contact point (A). A pressure space (12) is formed between the rotor (4) and the inner wall of the pump chamber (2) downstream from the contact point (A) in the direction of movement which is defined by the clockwise direction, and a suction space (11) is formed upstream from the contact point (A) in the direction of movement. A fluid can be drawn into the pump chamber (2) via the inlet (5) by the movement of the rotor (4) in the pump chamber (2). The separating element (8) connected to the rotor (4) and designed as a connecting rod is slightly inclined according to the position of the rotor (4).

Figure 3:
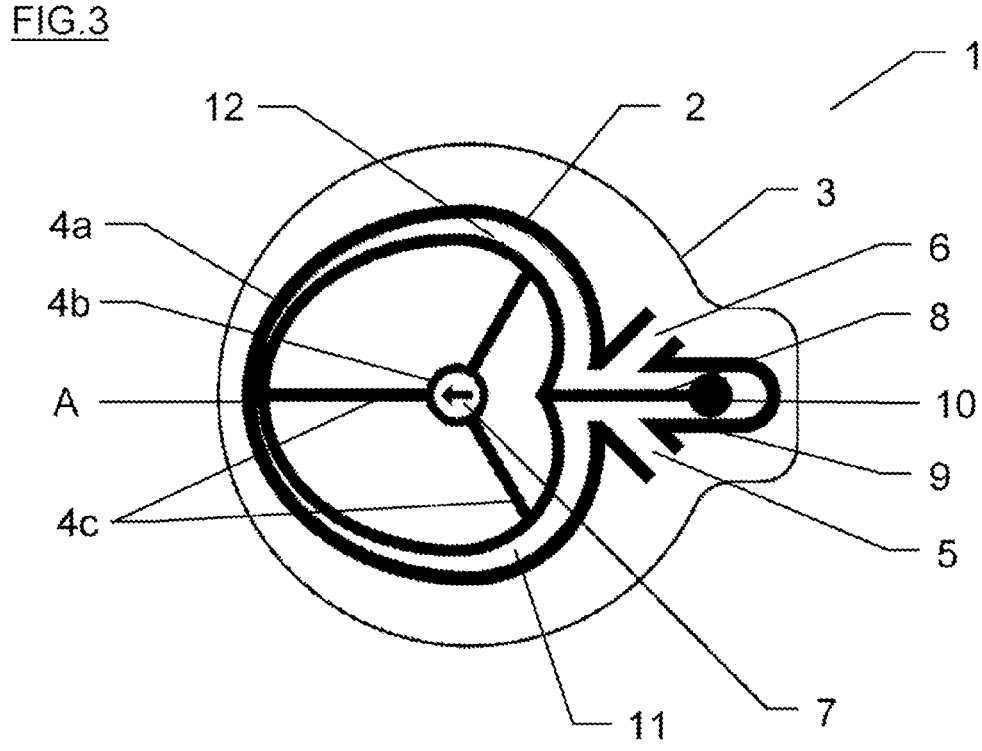
FIG. 3 shows a cross-section of a pump device according to the invention in the region of the pump chamber in the 180° angular position of the rotor.

The pump device (1) illustrated in FIGS. 1 and 2 is illustrated in FIG. 3 in a 180° angular position. In this position, the suction space (11) and the pressure space (12) are of the same size. The volume flow of a fluid flowing out of the outlet (6) of the pump device (1) reaches its maximum value in this position.

Figure 4:
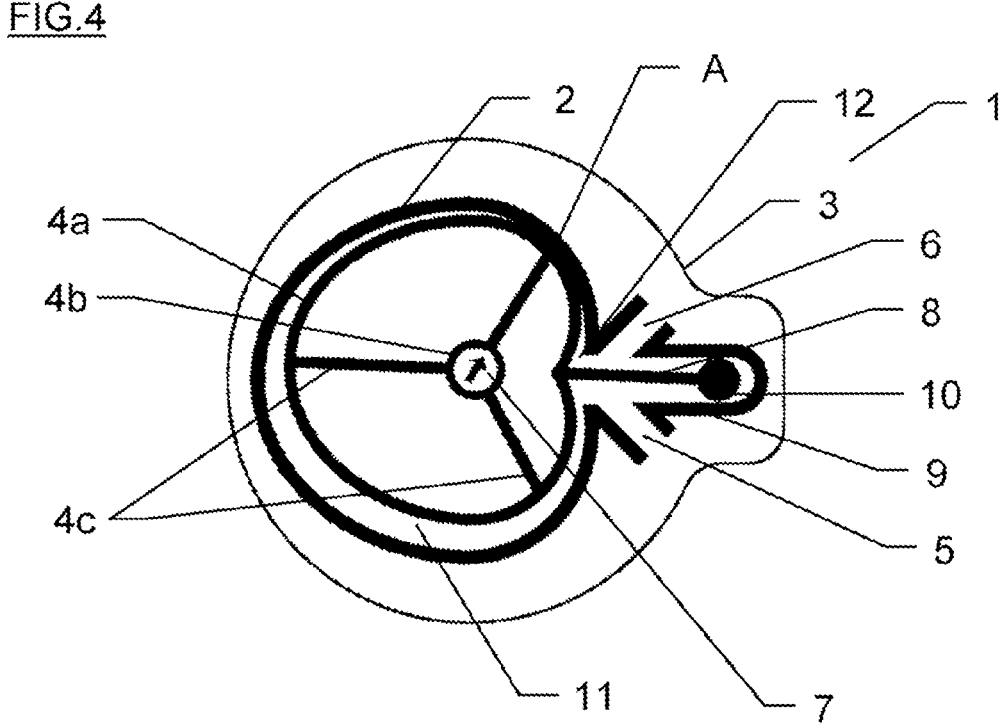
FIG. 4 shows a cross-section of a pump device according to the invention in the region of the pump chamber in the 300° angular position of the rotor.

The pump device (1) according to the invention shown in the previous drawings is illustrated in FIG. 4 in a 300° angular position. The suction space (11) then takes up the majority of the volume of the pump chamber (2), whilst the pressure space (12) now makes up only a very small part of it. The volume flow of a fluid flowing out from the pump device (1) via the outlet (6) is already approaching the minimum value.

The shape of the rotor (4) and the pump chamber (2) are matched to each other in such a way that two contact points (A, A') between the rotor wall (4a) and the inner wall of the pump chamber (2) are provided only in the 0° angular position on the orbital path of the rotor (4), whereas just one contact point (A) is provided in all other angular positions.

Figure 5:
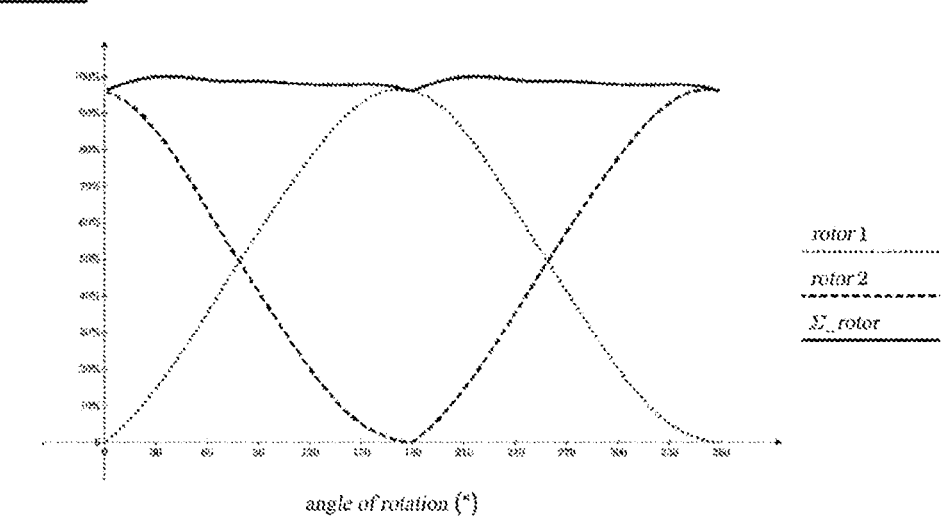
FIG. 5 shows a graph of the flow profiles of the fluid at the outlet of two pump chambers and a common outlet of both pump chambers.

The flow profile of a pump device (1) according to the invention with two pump chambers (2), in each of which a rotor (4) is arranged, is illustrated in FIG. 5, wherein the rotors (4) are driven phase-shifted relative to each other by 180°. The profile of the flow over the angular position corresponds in each case approximately to a sine wave, wherein for each pump chamber (2) the minimum value is 0% and the maximum value is more than 95% of the total volume flow. The cumulative flow profile (total volume flow) of a common outlet (6) to which the two pump chambers (2) are connected is also illustrated. The total flow of the pump device (1) is almost constant and varies only between approximately 95% and 100%.

Figure 6:
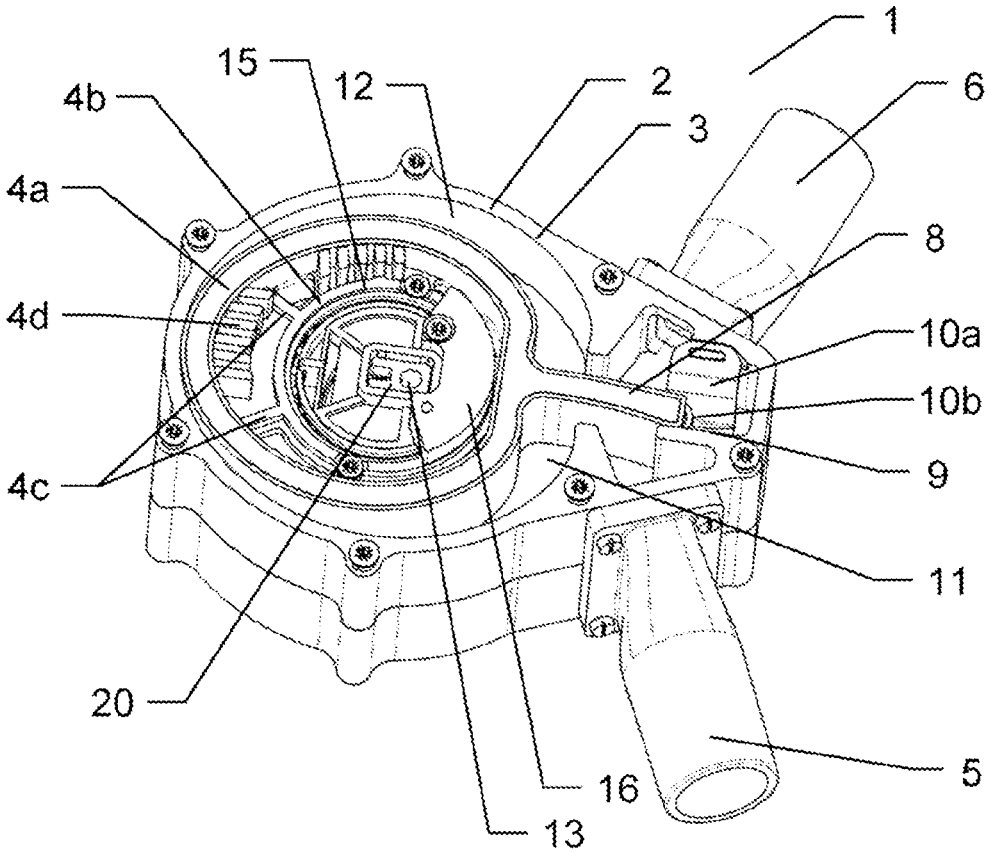
FIG. 6 shows a perspective view of a cross-section of a pump device according to the invention.

FIG. 6 shows a perspective view of a pump device (1) according to the invention, wherein a closure element, such as for example a sealed closure cap, sealing the pump chamber (2) at the top is not mounted so that the pump chamber (2) is open. The rotor (4) is situated approximately in the 180° angular position.

One end of the shaft (13) of the drive means (7) can be seen to which a decoupling apparatus (15) designed as a rolling bearing is connected via a connecting mechanism (20). The shaft (13) is here arranged eccentrically inside the decoupling apparatus (15) such that eccentric driving of the rotor (4) is effected. Also connected to the connecting mechanism (20) is a mass balancing element (16) by means of which the uneven mass distribution, which would otherwise create an imbalance when the shaft (13) rotates, can be compensated. The rotor core (4b) is connected to the rotor wall (4a) via spokes (4c). Arranged inside the rotor (4) are ribs (4d) which serve, together with the mass balancing element (16), to shift the center of gravity of the rotor (4) into the center of the rolling bearing used and/or into the middle of the motor axis or the shaft (13). Vibration is largely prevented or at least considerably suppressed as a result. A multi-part sealing element (10), which has a resilient counter bearing (10a) and a roller (10b), is arranged at that end of the separating element (8) which is averted from the rotor (4). By virtue of this arrangement, in case of doubt the separating element (8) can be pressed against the housing wall on the opposite side by the pressure at the outlet (6) so that the separating element (8) forms a seal against the housing. The spring-loaded running surface or the resilient counter bearing (10a) thus ensures a minimum contact pressure and the initial pressure also assists in case of doubt.

Figure 7:
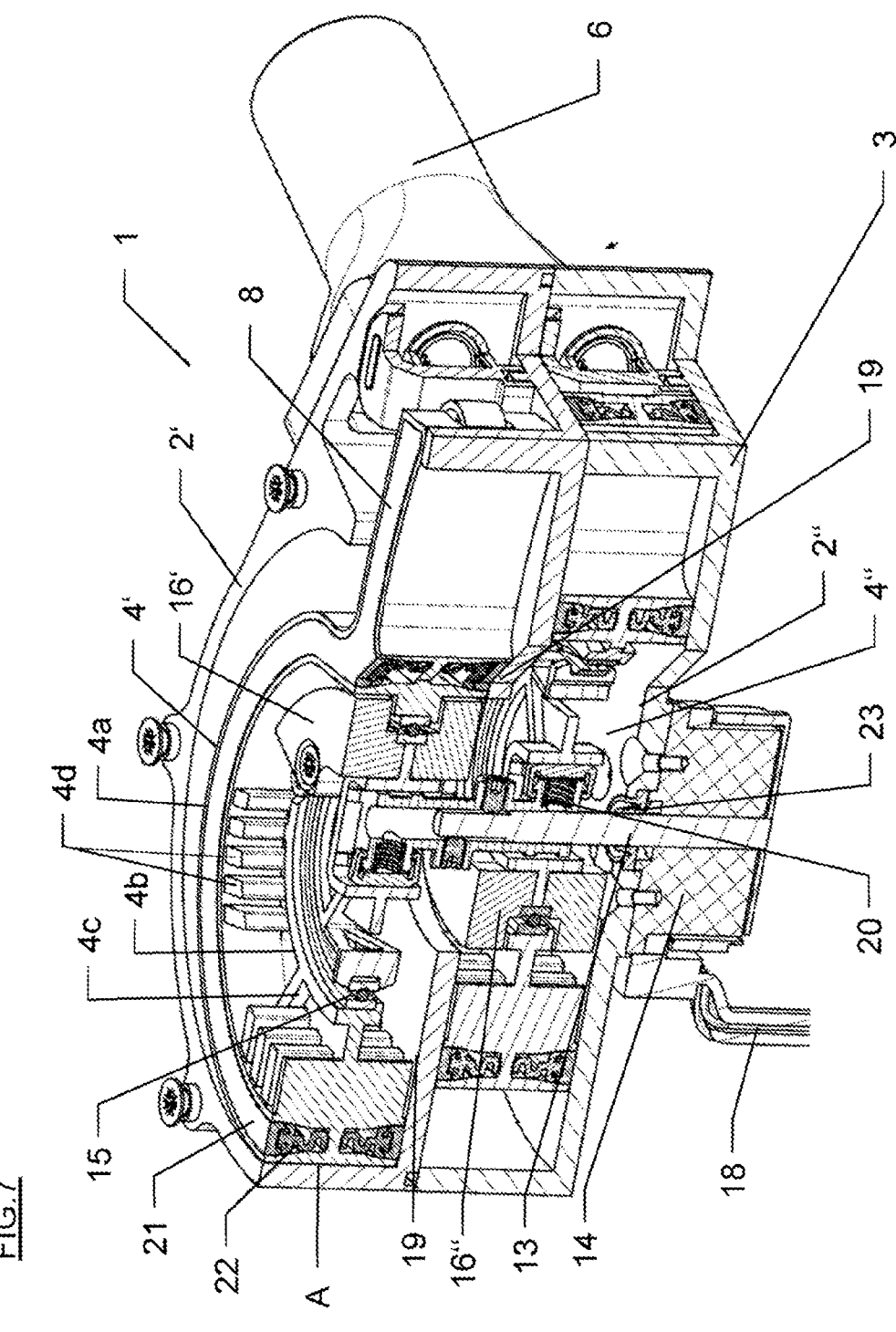
FIG. 7 shows a perspective view of a longitudinal section of a pump device according to the invention with two pump chambers and two rotors.

FIG. 7 shows in a schematic illustration a longitudinal section through an embodiment according to the invention of a pump device (1) having two pump chambers (2', 2") with in each case one associated rotor (4', 4"). The first rotor (4') is arranged in the first pump chamber (2') and is situated at approximately the 180° angular position. The second rotor (4") is arranged in the second pump chamber (2") and is situated at approximately the 0° angular position. The first pump chamber (2') is separated from the second pump chamber (2") by a separating wall (19). A motor (14), by means of which a shaft (13) can be driven, is furthermore arranged below the pump chambers (2', 2"). The shaft (13) is used to drive the two rotors (4', 4"). A decoupling apparatus (15) designed as a ball bearing is connected eccentrically on the shaft (13) in each case in the region of a pump chamber (2', 2") with the aid of a connecting mechanism (20) such that the rotors (4', 4") can be moved inside the pump chambers (2', 2") on orbital paths. The phase shift between the rotors (4', 4") is fixed at 180° by the orientation of the rotors (4', 4") on the shaft (13). A change in the phase shift during operation of the pump device (1) is thus excluded by the use of a common shaft (13). The mass balancing elements (16', 16") are likewise arranged offset to each other by 180°.

The rotors (4', 4") each have a sliding ring (21), which has a protrusion in the region of the separating element (8), at their ends in the axial direction. The sliding rings (21) are here each inserted into a circumferential groove, wherein the sliding rings (21) are not completely countersunk in the groove. The sliding rings (21) run against the walls bounding the pump chambers (2', 2") in the axial direction and thus seal the pump chambers (2', 2") relative to the interior of the respective rotor (4', 4"). In order to improve the sealing effect even in the case of increased component tolerances, the sliding rings (21) are spring-loaded by spring elements (22) in such a way wall. In the that they are pressed against the housing embodiment of the invention illustrated, the spring elements (22) lie behind the sliding rings (21) in the respective groove. The shaft (13) is sealed with the aid of a shaft seal (23).

In different embodiments of the invention, different positions of the motor (14) of the drive means are also conceivable, for example between the pump chambers (2', 2").

Figure 8:
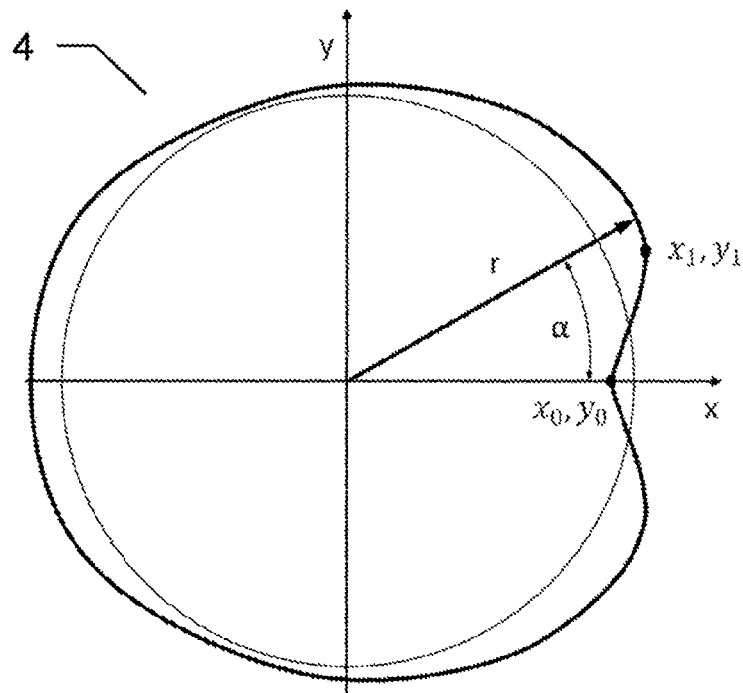
FIG. 8 shows a schematic illustration of the cross-section of a rotor of a device according to the invention.

A schematic illustration of the cross-section of a rotor (4) of a device (1) according to the invention is illustrated in FIG. 8. The shape of the rotor (4) is defined by a spline function. The radius r and the angle α by means of which the shape of the rotor (4) can be described in the illustrated coordinate system with an x-axis and y-axis are furthermore shown.

Figure 9:
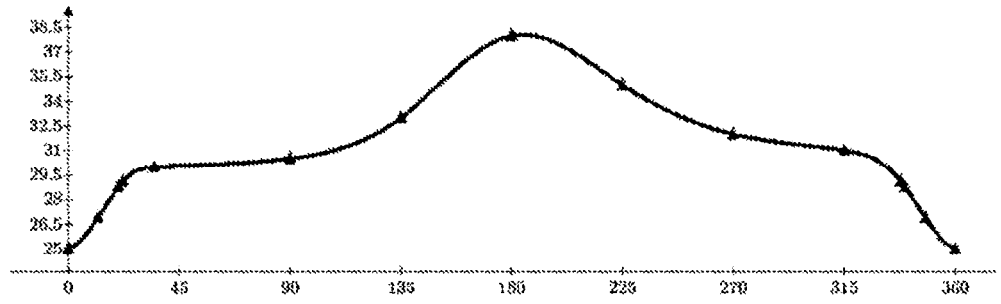
FIG. 9 shows the radial profile of the radius r of the rotor illustrated in FIG. 8 over the angle α.

FIG. 9 shows the profile of the radius r over the angle α of the rotor illustrated in FIG. 8. The triangles show which values (radius over angle) have been specified for the spline function (target points). The curve is a cubic spline function in the Cartesian coordinate system which is converted into the polar coordinate system.

The curve is not symmetrical about the central value of 180°, i.e. the rotor (4) of the corresponding embodiment of a device according to the invention is also not symmetrical about the x-axis. By optimizing the shape, the latter takes a form such that the flow of the out-flowing fluid is as constant as possible.

Figure 10:
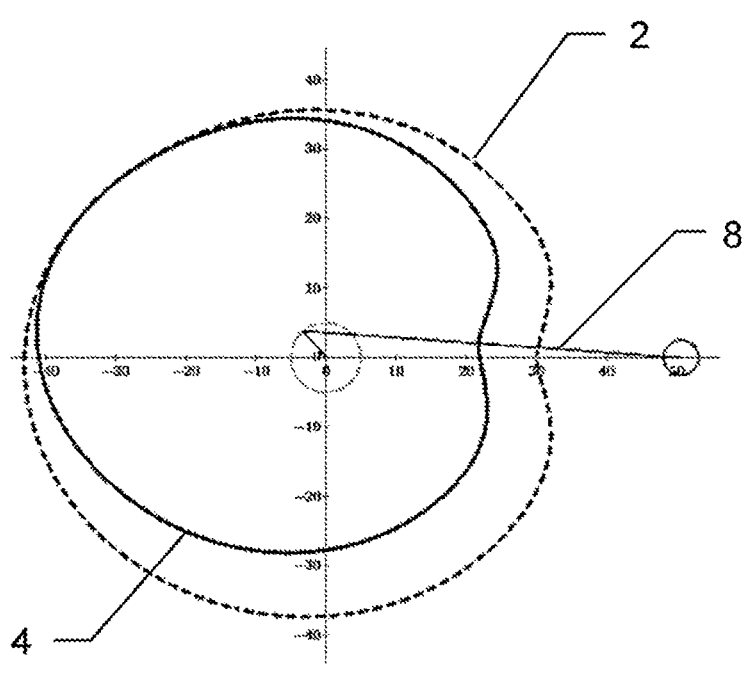
FIG. 10 shows a schematic illustration of the cross-section of a rotor in a pump chamber of a device according to the invention.

A schematic illustration of a cross-section of a rotor (4) shaped in accordance with a spline function in a correspondingly formed pump chamber (2) is illustrated in FIG. 10. The contour of the pump chamber (2) here results from the envelope of the rotor shape which is displaced over the crank angle according to the eccentric drive means over one complete revolution (0-360°).

The circle illustrated inside the rotor (4) is the circle of the eccentric center point.

Figure 11:
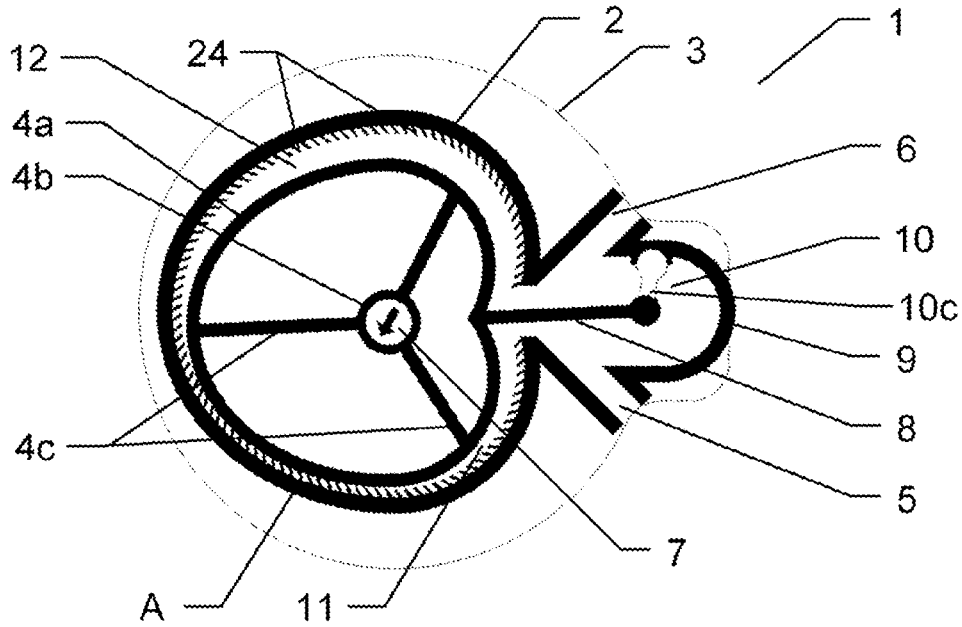
FIG. 11 shows a cross-section of a further embodiment according to the invention of a pump device.

FIG. 11 shows a cross-section of an embodiment of a pump device (1) according to the invention with a housing (3) of the pump chamber (2) which is designed so that it is resilient relative to the rotor (4).

For this purpose, the housing (3) has on its inside fins (24) which project into the pump chamber (2).

The fins (24) are positioned so that they are slightly inclined in the direction of movement of the rotor (4) in the embodiment illustrated. As a result, a low frictional force counteracting the movement of the rotor (4) is achieved with a simultaneously good sealing effect.

In such an embodiment of the invention, depending on the angular position of the rotor (4) in the pump chamber, there is no longer precisely one contact point (A) or there are no longer precisely two contact points and instead a contact region is formed around this point or these points in which the rotor (4) is contacted by a plurality of fins (24).

The embodiment illustrated of a pump device (1) according to the invention furthermore has a modification, which can also be implemented for all the other embodiments shown, of the sealing element (10) which connects the separating element (8) to the housing (3) of the pump chamber (2) on its side averted from the rotor (4) in sealing fashion. The sealing element (10) here has a lever (10c) which is mounted on the housing (13) so that it can move in rotation about a first axis of rotation and which is connected to the end of the separating element (8) so that it can move in rotation about a second axis of rotation such that, in contrast to the design as a connecting rod mounted in sealing fashion in a guide (9), a lower friction occurs in this region.

The sequence of a method according to the invention for providing respiratory gas is illustrated schematically in FIG. 12. In the case of the use of a pump device according to the invention with a housing spring-mounted relative to the rotor, instead of the contact point or the contact points, contact regions extending around these points are formed
between the rotor and the housing.

The invention claimed is:

1. A respiratory device comprising at least one pump
device, comprising: at least two pump chambers and, for
each pump chamber, a rotor arranged in the pump chamber,
the at least one pump chamber having an inlet and an outlet
so that a fluid can flow into the pump chamber via the inlet
and can flow out of the pump chamber via the outlet,
wherein the inlet and the outlet are connected to the pump
chamber by a common duct, wherein a separating element is
arranged in the duct to separate the inlet from the outlet,
wherein the rotor is drivable on an orbital path inside the
pump chamber, wherein the rotor and the pump chamber are
shaped to match each other so that an approximately sinu-
soidal profile of the flow of the fluid flowing out of the outlet
is effected by movement of the rotor in the pump chamber
at a constant speed, wherein the rotors are arranged in the
pump chambers, phase-shifted relative to each other by 180°
and wherein the two pump chambers have a common outlet
at which the approximately sinusoidal flows of respective
out-flowing fluids join together to form a cumulative sub-
stantially constant total flow.

2. The respiratory device according to claim 1, further
comprising eccentric drive means for moving the rotor on
the orbital path.

3. The respiratory device according to claim 1, wherein
the shape of the rotor and the shape of the pump chamber are
matched to each other so that, when considering a cross-
section in the 0° angular position of the rotor inside the
pump chamber, two contact points or two contact regions
arranged about these contact points are formed between the
rotor and an inner wall of the pump chamber, and in all other
angular positions, just one contact point or one contact
region arranged about the one contact point is formed
between the rotor and the inner wall of the pump chamber.

4. The respiratory device according to claim 1, wherein
the separating element is connected to the rotor and projects
from the rotor into a region of the inlet and the outlet.

5. The respiratory device according to claim 1, further
comprising a housing, wherein the rotor is spring-mounted
relative to the housing.

6. The respiratory device according to claim 1, further
comprising a housing, wherein the housing is spring-
mounted relative to the rotor.

7. The respiratory device according to claim 6, wherein
the housing has fins that project inward into the pump
chamber and extend transversely to a direction of movement
of the rotor.

8. The respiratory device according to claim 1, further
comprising a common shaft arranged to drive the rotors.

9. A method for providing respiratory gas, comprising the
steps of: displacing a rotor in a pump chamber from a 0°
angular position, in which the rotor has two contact points,
or two contact regions arranged around these contact points,
with an inner wall of the pump chamber and consequently
ceiling an inlet region and an outlet region relative to a
remainder of the pump chamber, in a direction of movement
of the rotor on an orbital path, into a position in which the
rotor and the inner wall of the pump chamber have precisely
one contact point, or one contact region arranged around the
contact point; separating a pressure space in front of the
rotor in the direction of movement and a suction space
behind the rotor in the direction of movement by the contact
point of the rotor and the inner wall of the pump chamber;
drawing respiratory gas from the inlet into the suction space;
and delivering the respiratory gas from the pressure space
via the outlet by continuous displacement of the rotor in the
pump chamber, wherein the method steps are implemented
in a sequence phase-shifted by 180° with a second rotor in
a second pump chamber so that, when the rotors circulate on
the respective orbital paths inside the respective pump
chamber at a constant running speed, an optimally smooth
flow profile of the respiratory gas is achieved at a common
outlet, including using a respiratory device according to
claim 1 to carry out the method steps.

10. The respiratory device according to claim 1, wherein
the shape of the rotor is designed in cross-section according
to a spline function generated in cartesian coordinates and
transferred to polar coordinates, so that a curve progression
without jumps is enabled.

11. The respiratory device according to claim 10, wherein
the spline function is formed from cubic parabolas.

* * * * *